United States Patent [19]
Joseph et al.

[11] Patent Number: 5,324,426
[45] Date of Patent: Jun. 28, 1994

[54] CHROMATOGRAPHY COLUMN

[75] Inventors: Thomas Joseph, Macungie, Pa.;
Alfred J. Pearson, Princeton, Mass.;
Robert C. Adams, Millville; Omar A.
Swift, Vineland, both of N.J.

[73] Assignee: Kontes Glass Corp., Vineland, N.J.

[21] Appl. No.: 855,095

[22] Filed: Mar. 20, 1992

[51] Int. Cl.⁵ .............................................. B01D 15/08
[52] U.S. Cl. .................... 210/198.2; 210/456;
210/656; 96/105; 96/107
[58] Field of Search ............ 210/656, 658, 659, 198.2,
210/198.3, 456; 55/67, 386; 96/105, 107

[56] References Cited

U.S. PATENT DOCUMENTS

| D. 309,498 | 7/1990 | Colvin | D24/8 |
| 3,361,261 | 1/1968 | Fairey | 210/446 |
| 3,483,986 | 12/1969 | Wright | 210/198.2 |
| 3,487,938 | 1/1970 | Patterson | 210/198.2 |
| 4,225,440 | 9/1980 | Pitesky | 210/445 |
| 4,350,595 | 9/1982 | Gunkel | 210/198.2 |
| 4,354,932 | 10/1982 | McNeil | 210/198.2 |
| 4,557,830 | 12/1985 | Onitsuka | 210/286 |
| 4,582,608 | 4/1986 | Ritacco | 210/198.2 |
| 4,597,866 | 7/1986 | Couillard | 210/198.2 |
| 4,636,315 | 1/1987 | Allen | 210/198.2 |
| 4,670,141 | 6/1987 | Shackelford | 210/198.2 |
| 4,719,011 | 1/1988 | Shalon | 210/198.2 |
| 4,737,292 | 4/1988 | Ritacco | 210/198.2 |
| 4,792,395 | 12/1988 | Lee | 210/198.2 |
| 4,797,209 | 1/1989 | Jackson | 210/198.2 |
| 4,882,047 | 11/1989 | Shalon | 210/198.2 |
| 4,888,112 | 12/1989 | Kronwald | 210/198.2 |
| 4,891,133 | 1/1990 | Colvin | 210/198.2 |
| 4,894,152 | 1/1990 | Colvin | 210/198.2 |
| 4,986,909 | 1/1991 | Rai | 210/198.2 |
| 5,013,433 | 5/1991 | Shalon | 210/198.2 |
| 5,021,162 | 6/1991 | Sakamoto | 210/198.2 |
| 5,141,635 | 8/1992 | Le Plang | 210/198.2 |

Primary Examiner—Ernest G. Therkorn
Attorney, Agent, or Firm—James & Franklin

[57] ABSTRACT

In a chromatography column one or more of the end plates defining the column are provided with specially designed lands and grooves to more effectively uniformly distribute the input liquid over the column cross-sectional area and thus improve the separation of sample components, the upper end wall of the column being adjustably positionable to vary the axial length of the column by means of novel structure including readily releasable speed nuts engageable with externally threaded rods, the seal between the movable upper plate and the column wall being so designed as to minimize dead space and thus further increase separating power, and the structure for adjustably positioning said top wall includes elements enabling that structure and the top wall connected thereto to be conveniently supported in inverted condition when separated from the remainder of the column structure.

11 Claims, 6 Drawing Sheets

CHROMATOGRAPHY COLUMN

The present invention relates to the construction of a chromatography column of adjustable height which has improved analytical characteristics. Cooperative features of the construction effectively ensure that sample and mobile phase fluid is substantially uniformly distributed over the cross-section of the column, height adjustment of the column is very readily effected, the movable column end wall seals to the column proper in a manner minimizing dead space, and the position-adjusting structure for the movable end wall is so constructed that the subassembly may readily be placed in an inverted standby condition when the top wall is removed from the column.

BACKGROUND OF THE INVENTION

Chromatographic columns are used for the purification, characterization, analysis or preparation of molecular mixtures. Usually the column is packed with a suitable chromatographic packing material, the column is equilibrated with a suitable mobile phase (aqueous or organic), the sample is loaded onto the packing material in the column and the mobile phase is then used to selectively elute discrete molecular species.

In the most rudimentary sense, the column serves to contain the packing material, filters usually being provided at the column inlet and outlet. The mobile phase enters the column through a small diameter opening at high linear velocity, passes through the large diameter column at a relatively low linear velocity, and then exits the column at high linear velocity through a small diameter opening. These changes in flow, cross-sectional area and linear velocity make it difficult to avoid the problems presented by mixing or turbulence of the mobile phase and the presence of dead volume or stagnant areas.

The performance of liquid chromatography separations in column configurations is dependent on the distribution (direction and local linear velocities) of fluid into the column, particularly at the location where the liquid initially impacts the column packing material. The distribution of incoming liquid affects column capacity and efficiency which control the amount of material that can be processed (throughput) and the ability to separate closely related substances (resolution).

In analytical separations (where sample mass is small and the intention is to maximize resolution) column load is typically well below the total binding capacity of the column's packing material. Only a small percentage of the column's total binding capacity is typically used. Because throughput is not of concern in analytical separations, full utilization of total binding capacity is not generally maximized.

In preparative separations, however, the objective is to maximize throughput at an acceptable level of resolution. In an ideal situation both throughput and resolution would be at their independent maximum levels. However, because of the relationship between sample mass, efficiency and economics a trade-off is usually made. In practice, sample mass (load) is increased until an unacceptable reduction in efficiency and resolution is noted. To achieve optimum results in terms of both throughput and resolution, utilization of the column's total binding capacity needs to be maximized. Distribution of fluid onto the column packing material affects utilization of total binding capacity and will substantially affect both throughput and resolution as a function of load.

The predominant effect of increasing load is increased peak width due to local (column inlet) saturation of the packing material's binding sites. Local saturation prevents new sample molecules entering the column from interacting with the packing material at the column entry point. Sample must travel deeper into the column, causing dilution and loss of efficiency. Also, due to fewer interactions with the packing material, separation of the various molecular species is decreased.

Localized saturation can be mitigated by multipoint distribution of sample and mobile phase onto the packing material in the column. In this way, a larger portion of the packing material in the column is utilized.

SUMMARY OF THE INVENTION

A major element of the invention described herein is the uniform and even multipoint distribution of the fluid entering the column, which is accomplished with minimal mixing as the fluid travels from narrow bore tubing at high linear velocity to the wide bore of the column at low linear velocity. The structure of the present invention provides a novel multipoint distribution system which maintains efficiency under both low and high loading conditions. This multipoint distribution system is preferred for applications in preparative chromatography.

In order to maximize throughput without sacrificing resolution, and hence render the column excellently effective for preparative separations, a multipoint distribution of sample and mobile phase onto the packing material in the column is desirable. The ultimate in multipoint distribution is a substantially uniform distribution of the entering fluid over the entire cross-sectional area of the column. It is most desirable that this be accomplished with minimal mixing, which is a problem because the fluid travels from a narrow bore input at high linear velocity to the wide bore of the column at low linear velocity. In addition, when the liquid leaves the column it travels in an opposite sense from the wide bore of the column at low linear velocity to a narrow bore outlet at high linear velocity, so that minimum resistance to flow is important. In accordance with the present invention the column-facing surfaces of the column end walls are provided with fluid-distributing channels (grooves between lands) so designed as to maximize uniform fluid distribution over the entire cross-sectional area of the column at its upper or fluid-entrance end and to optimize fluid flow-out from the column at its lower or fluid-exit end.

Another important factor in the design of a chromatographic column is to eliminate as much dead space as possible. Dead space is space where liquid entering the column may reside without passing through the column. In accordance with the present invention dead space at the end of the column that carries a wall movable to vary the length of the column is minimized through a novel orientation of the surfaces engaging the operative sealing ring, so that when that wall has been positioned and is to be sealed to the column wall, the ring, compressed between axially movable parts of the top wall to seal to the column wall, also acts to reduce dead space. Also, the occurrence of dead space at the bottom wall is minimized through the specific shaping of distribution grooves formed in the column-facing surface of that bottom wall.

When a given column is designed to have an adjustable height, means must be provided for properly locating the movable end wall of the column so that the desired relationship between that wall and the column content can be readily achieved. In the column of the present invention the position of the movable end wall is adjusted by the interaction of externally threaded members with readily releasable speed nuts.

When a given adjustable column is to be filled or emptied the movable top wall of the column must be removed to provide access to the column proper, and that top wall must then be placed aside while the filling of the then open-ended column takes place. Because of the delicacy and precision of the analytical or preparative process to be carried out, and because the end surface of the then-exposed column top wall must therefore be kept in proper condition, the subassembly of the present invention which comprises that movable top wall and the structure employed to adjustably position that top wall is provided in effect with legs which enable that subassembly to stand on a floor in inverted condition, thus preventing contact between the exposed top wall and possibly adulterating media.

It is therefore a prime object of the present invention to devise a chromatography column in which the incoming fluid is more effectively uniformly dispersed over the cross-sectional area of the column than has previously been accomplished, the flow of fluid from the column to the outlet is optimized to minimize flow resistance and eliminate dead space, the amount of dead space at an adjustably positionable end wall is minimized, the adjustable positioning of that end wall to create columns of different length is facilitated, and the end wall, when removed from the column so that the column may be emptied or filled, can be safely supported in an accessible but protected fashion. These various aspects of the column construction cooperate to achieve the generalized object of the present invention, which is to devise a chromatography column of improved effectiveness, particularly for a preparative separation, and which preferably is of readily adjustable effective length.

BRIEF DESCRIPTION OF THE DRAWINGS

To the accomplishment of the above, and to such other objects as may hereinafter appear, the present invention relates to the construction of a chromatography column as defined in the appended claims and as described in this specification, taken together with the accompanying drawings in which:

DESCRIPTION OF THE PREFERRED EMBODIMENT

Figure 1:
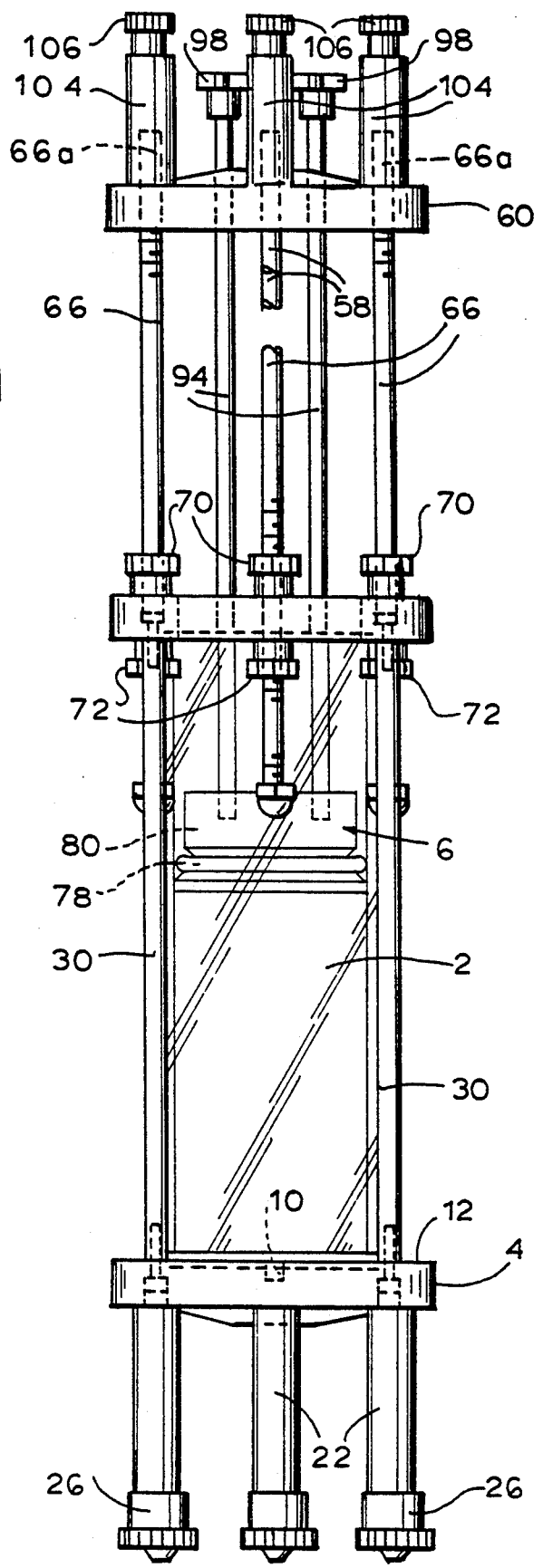
FIG. 1 is an elevational view of one embodiment of the present invention, the column-producing wall being shown as made of transparent glass.
Figure 2:
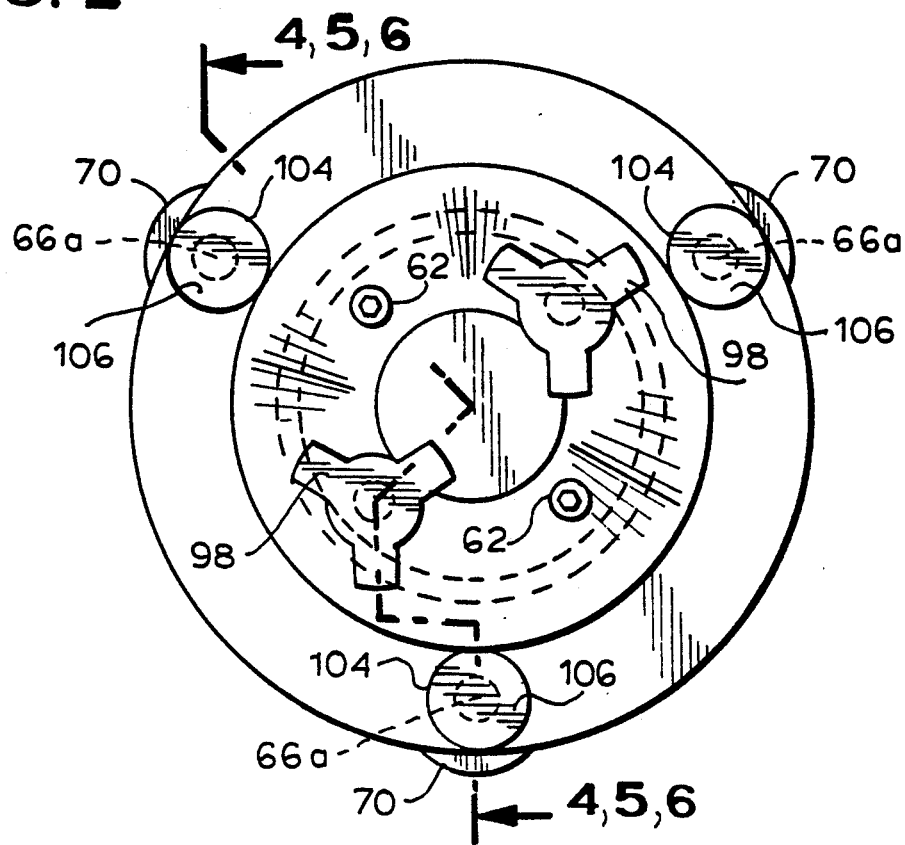
FIG. 2 is a top plan view of the column of FIG. 1.
Figure 3:
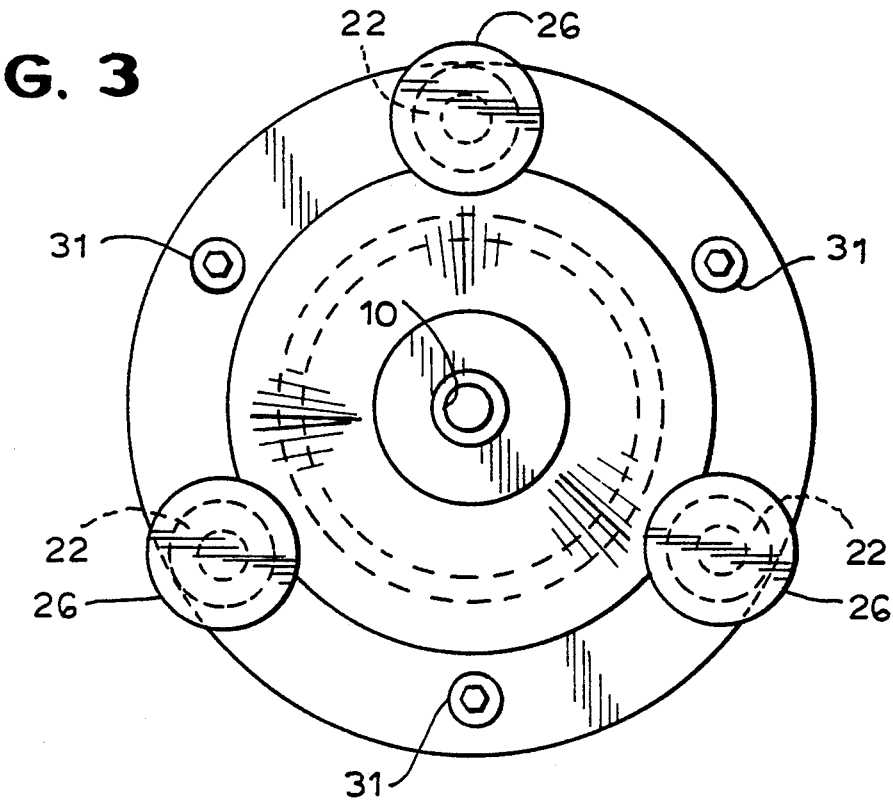
FIG. 3 is a bottom plan view thereof.

In the specific embodiment of the present invention here illustrated the column proper is defined by a cylindrical wall 2 of appreciable internal diameter, a fixed bottom wall 4 on which the cylindrical wall 2 is sealingly mounted, and an adjustably movable top wall 6 which is received inside the cylindrical wall 2 so as to be adjustably positionable axially therealong and to sealingly engage the inner surface of the wall 2. The space between the walls 4 and 6 is adapted to be filled with a suitable packing material, and the mobile phase enters the column through a relatively narrow inlet passage 8 in the top wall 6 and leaves the column through a relatively narrow outlet passage 10 in the bottom wall 4.

Figure 5:
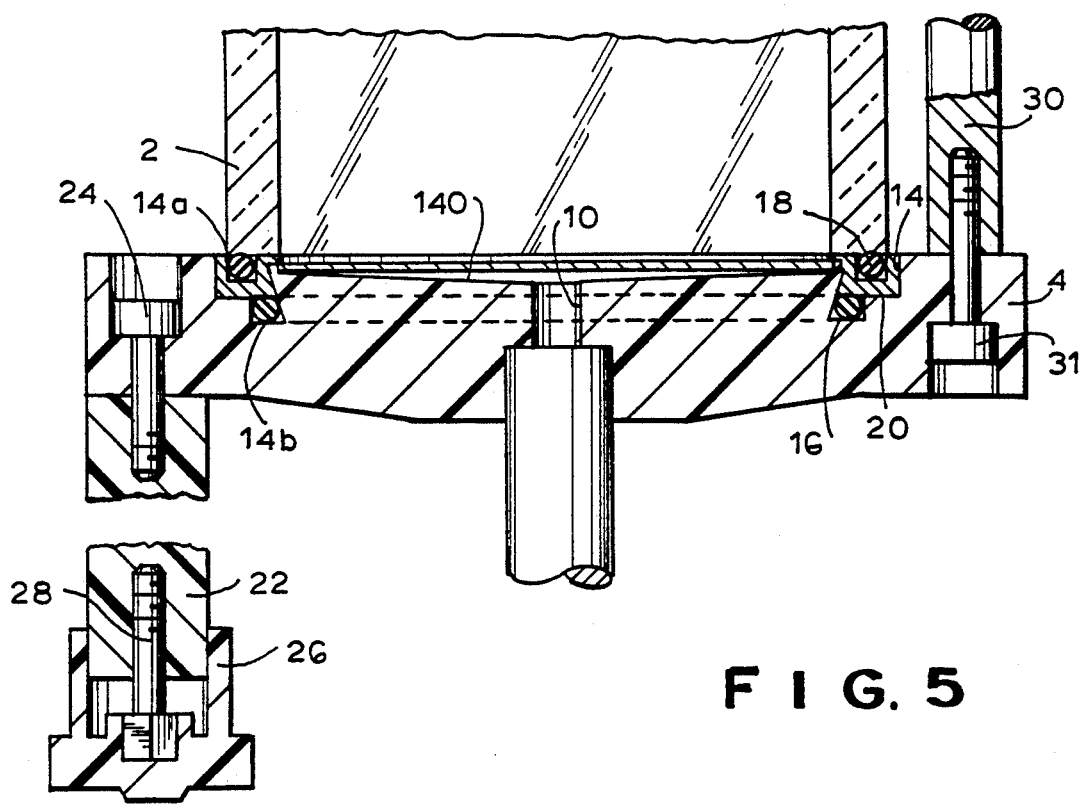
FIG. 5 is a cross-sectional view of the lowermost horizontal wall of the column taken along the line 5—5 of FIG. 2.

The upper surface 12 of the bottom wall 4 is provided with a groove 14 into which one end of the cylindrical wall 2 is received, and that groove is provided with suitable sealing and packing material, such as a rubber O-ring, so as to produce a seal between the walls 2 and 4. As here disclosed and as may best be seen in FIG. 5, the groove 14 consists of an upper section 14a and a lower section 14b, with an O-ring 16 received in the section 14b and with an O-ring 18 contained within a shaped packing ring 20 being received in the groove section 14a, the lower end of the wall 2 engaging the upper surface of the rings 18 and 20. The bottom wall 4 is provided with a plurality of depending legs 22 secured to the wall 4 by screws 24, and those legs are provided with adjustable telescoping feet 26 in turn secured in place by screws 28, so that the entire column assembly may be mounted in level condition on a suitable supporting surface such as a table.

Extending up from the radially outer portions of the bottom wall 4 are a plurality of rods 30 fixed to the wall 4 by screws 31, and a structural ring 32 is fixed to the upper ends of those rods 30 so as to rest on the top of the wall 2, the upper end of that wall 2 being received in a groove 34 in the downwardly facing surface of the ring 32, a sealing ring 36 being received in that groove and adapted to be engaged by the upper edge of the wall 2 so as to form a seal. The radially inner opening of the ring 32 has a diameter at least equal to that of the wall 32 so as not to inhibit access to the column through the open top of that wall 2. The ring 32 is secured to the upper ends of the rods 30, as by screws 40, thereby to secure the cylindrical wall 2 in sealed relationship with the bottom wall 4.

Figure 6:
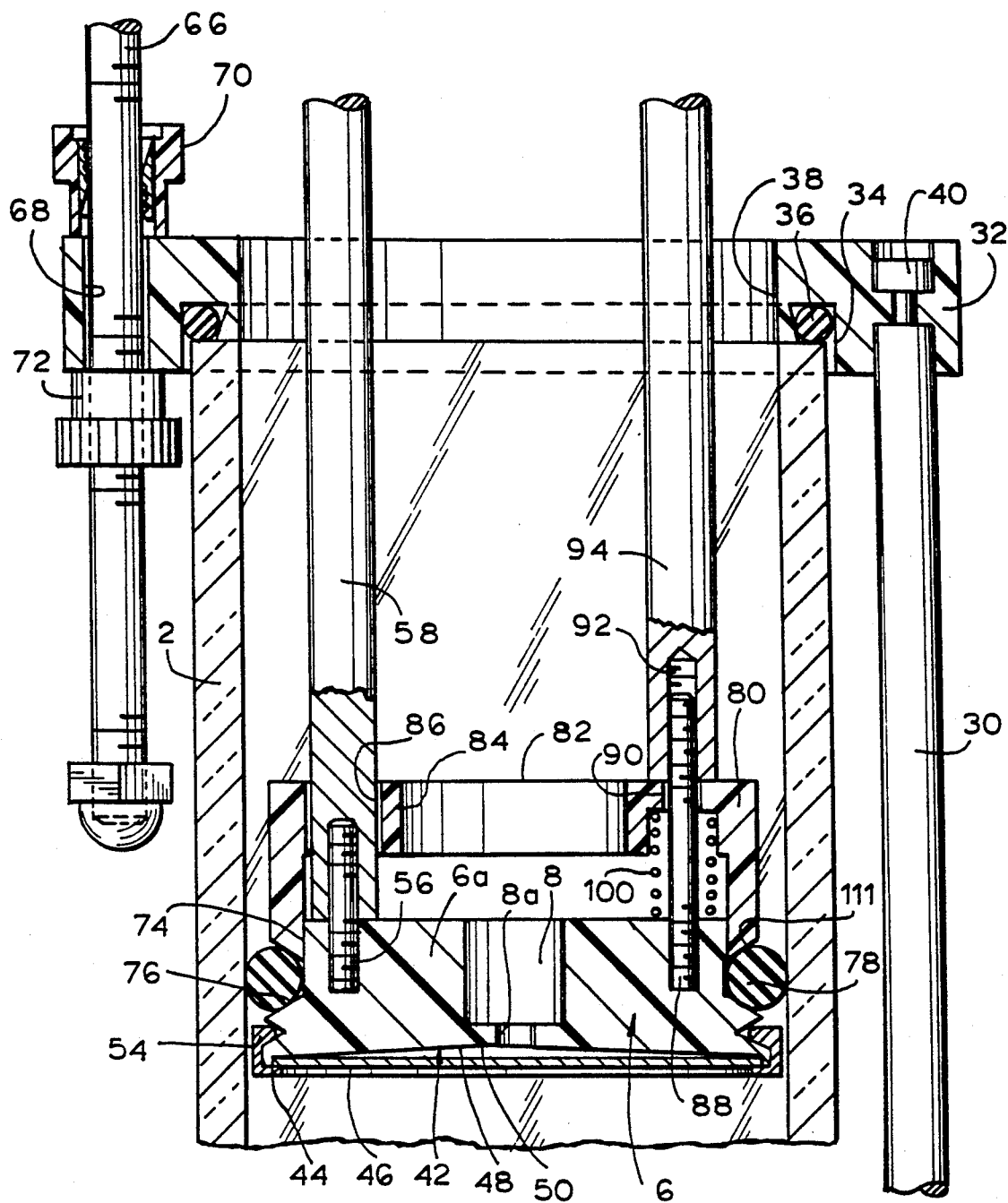
FIG. 6 is a cross-sectional view of the intermediate horizontal wall and the movable top wall of the column, taken along the line 6—6 of FIG. 2.
Figure 7:
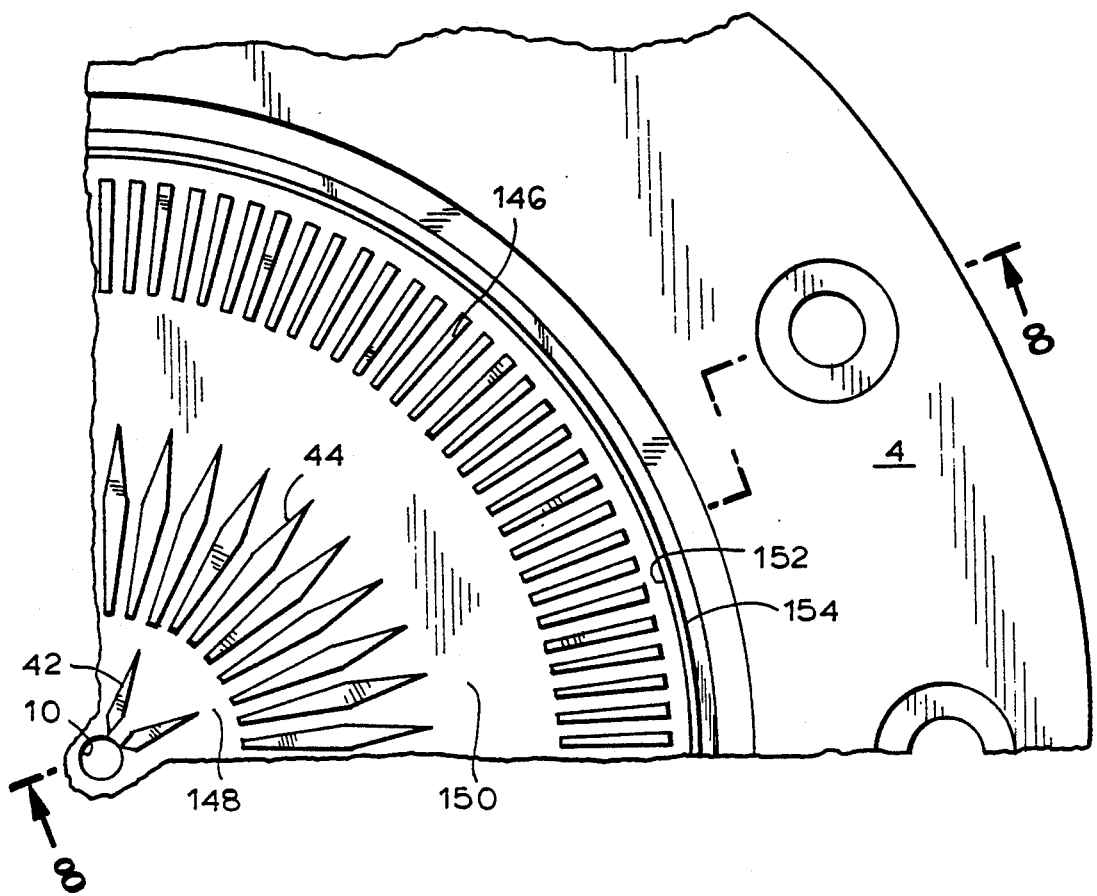
FIG. 7 is a top plan view of a portion of the column-facing surface of the lower column wall.
Figure 8:
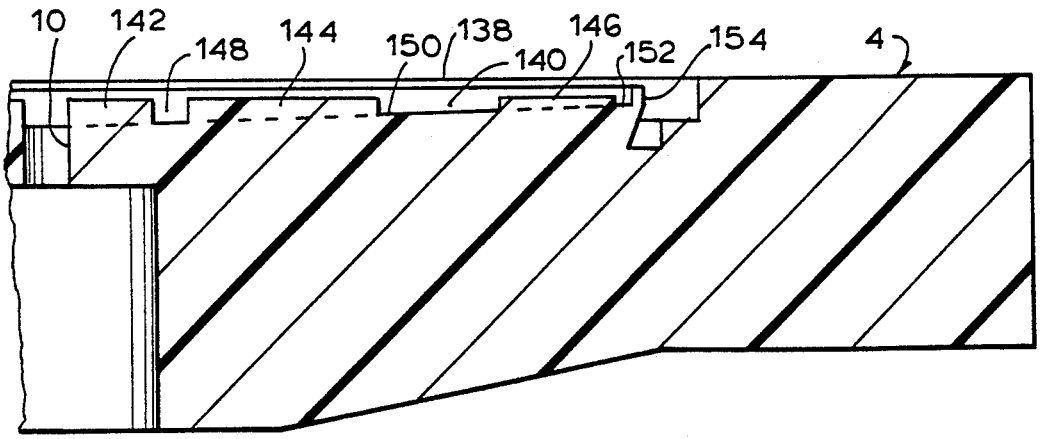
FIG. 8 is a cross-sectional view taken along the line 8—8 of FIG. 7.

Details of the adjustably positionable upper column wall 6 may perhaps best be seen from FIG. 6. The wall 6 has a diameter somewhat less than the inner diameter of the cylinder 2 so that the wall 6 can readily be moved axially to a desired position relative to the bottom wall 4. Its lower column-facing surface 42 is defined by a lower recessed section 44 within which a filter 46 of appropriate nature may be received, by an upwardly and inwardly inclined section 48, and by a central flat section 50 carrying a plug 51 pierced by four circumferentially spaced vertical holes 52 which in turn communicate with the lower reduced diameter portion 8a of the central inlet orifice 8. A retaining ring 54 holds the filter 46 in place.

Secured to the wall 6 by studs 56 and extending up therefrom are rods 58 which project up beyond the upper end of the wall 2 and are secured to wall 60 by screws 62. Thus movement of the wall 60 causes corresponding movement of the wall 6. The radially outer portions of the wall 60, located radially beyond the wall 2, have apertures 64 through which elongated externally threaded rods 66 pass in threaded engagement, those rods 66 extending down through apertures 68 in that portion of the ring 32 which extends radially out beyond the wall 2. The rods 66 are freely axially movable through the apertures 68 as the wall 60, and hence the wall 6, are moved. Two sets of speed nuts 70 and 72 are mounted on the rods 66, the set 70 being located above ring 32 and the set 72 being located below the ring 32. The characteristic of these speed nuts 70 and 72, which are known products, is that when rotated in one direction they will engage and lock themselves onto the threaded rods 66 but when rotated in the other direction the threaded engagement will disengage so that the nuts can be moved axially along the length of the rods 66. The function of the speed nuts 70 and 72 is to fix the axial position of the rods 66 relative to the ring 32 through which they pass, thereby to fix the axial location of the column top wall 6 which is rigidly connected to the rods 66. Assuming that the wall 6 has been fixed in position, with the speed nuts 70 engaging the upper surface of ring 32 and the speed nuts 72 engaging its lower surface, if the wall 6 is to be lowered the upper set of speed nuts 70 are rotated to effect disengagement, the wall 60 is lowered to bring the wall 6 to its new position, thus lowering the speed nuts 72 from the ring 32, the speed nuts 70 are then moved down to the upper surface of the ring 32, and they are then rotated to re-engage with the rods 66 thus preventing the wall 6 from moving downwardly any farther. The speed nuts 72 are then moved upwardly into engagement with the lower surface of ring 32, and re-engaged with the rods 66 so as to prevent the wall 6 from moving up from its desired position. When the wall 6 is to be raised the sequence of operations is reversed. As a result the wall 6, when placed in position, is reliably held in that position, and adjustment of its position can be accomplished quickly and easily.

If the wall 6 is to be readily moved axially of the column it cannot firmly engage the interior of the column, but when the column is being used it is essential that there be an effective seal between the wall 6 and the wall 2 so that fluid does not escape around the column top. Moreover, analytical use of the column requires close control of the fluid flowing therethrough, to the end that all of the fluid that enters the column leaves the column in due course and as little as possible of the fluid that enters the column remains stagnant therein. The space where fluid can remain stagnant within the column is generally termed "dead space", and minimization of the volume of that dead space is an important factor in achieving a high degree of analytical accuracy.

To meet these requirements the wall 6 is provided with an upper portion 6a of reduced diameter to produce a radially outwardly facing surface 74 and a downwardly and outwardly inclined surface 76, while the maximum outer diameter of the wall 6, together with the retaining ring 54, is less than the internal diameter of the wall 2. A compressible sealing ring 78 is received around the surface 74 and on the downwardly and outwardly inclined surface 76. Telescopically mounted on the surface 74 above the sealing ring 78 is a cup 80 the horizontal portion 82 of which is provided with a central aperture 84 giving access to the inlet opening 8 and with apertures 86 through which the rods 58 freely pass. Threadedly fixedly received in the wall 6 and extending up therefrom are a plurality of studs 88, which studs extend freely through apertures 90 in the wall 82 and are received within internally threaded axial apertures 92 at the lower ends of upwardly extending rods 94. Those rods 94 extend freely through apertures 96 in the wall 60 and extend up above the wall 60, where handles 98 are secured to them. Springs 100 are compressed between the walls 6 and 8. The lower sealing-ring-engaging surface 101 of the cup 80 is upwardly and outwardly inclined.

When the upper wall 6 is to be axially moved within the wall 2 the handles 98 are turned so as to rotate the rods 94 and withdraw them from the upper ends of the studs 88, thus permitting the cup 80 to move upwardly as urged by the springs 100, and this in turn releases axial pressure on the sealing ring 78 so that said ring is not pushed against the internal surface of the wall 2. This renders the wall 6 readily slidable up and down within the wall 2. When the wall 6 is in its desired position the handles 98 are rotated so as to move the rods 94 down along the studs 88, and this in turn pushes the ring 80 down against the action of the spring 100, compressing the sealing ring 78 between the surfaces 76 and 100, thus causing the ring 78 to sealingly engage the inner surface of the wall 2. Particularly because of the orientation of the downwardly and outwardly inclined surface 76 the sealing ring 78 is not only urged outwardly into engagement with the inner surface of the wall 2 but is also urged downwardly toward the packing ring 54. Since the volume around the wall 6 below the sealing ring 78 constitutes a space which liquid will enter and not leave, in other words a dead space, the fact that the sealing ring 78 is moved axially downwardly as well as radially outwardly when sealing is effected significantly reduces the volume of that dead space, and thus affirmatively improves the analytical accuracy of the column.

Figure 4:
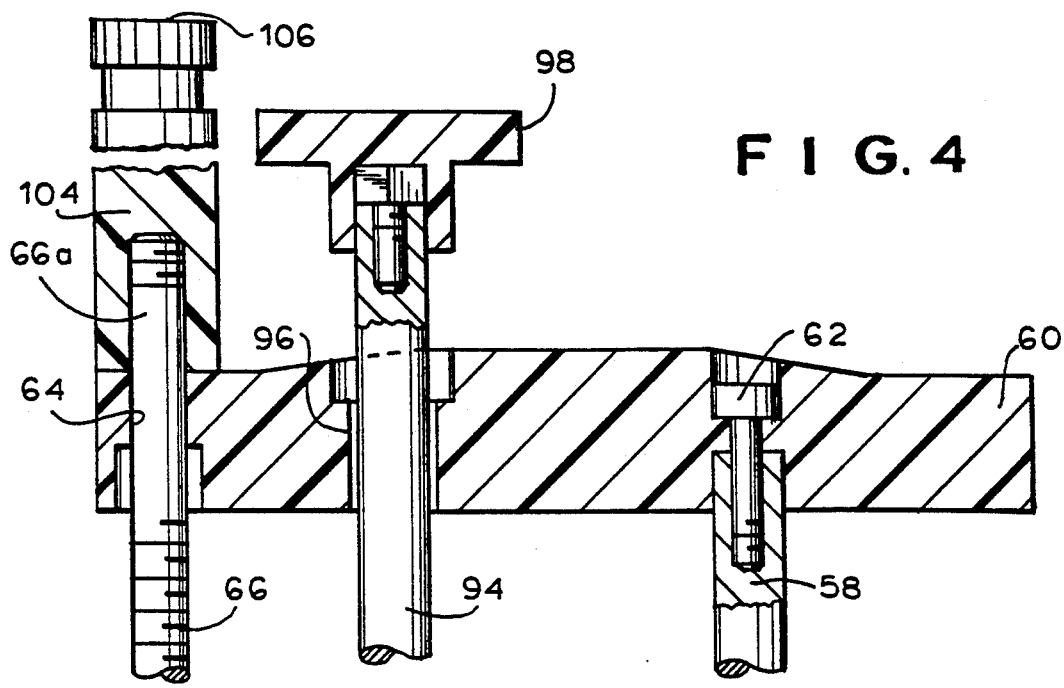
FIG. 4 is a cross-sectional view of the uppermost horizontal wall of the column taken along line 4—4 of FIG. 2.

When access to the interior of the column is desired, as for insertion or removal of the packing material, the bottom wall 6 is withdrawn from the open top of the column by lifting the wall 60 to which it is connected. The assembly of the wall 60, the wall 6 and associated structure must then be put aside until closing of the upper end of the column is desired. At the same time care must be taken not to adulterate the exposed lower surface 48 of the wall 6 or the filter 46 when it is in place. To that end the externally threaded rods 66 which connect the wall 60 to the ring 32 have portions 66a which extend upwardly beyond the wall 60, and cylinders 104 are threadedly received thereover, those cylinders, as may be seen from FIGS. 1 and 4, extending upwardly beyond the handles 98. Hence the exposed upper surfaces 106 of those cylinders 104 constitute supports or feet for the bottom wall assembly when it has been removed from the cylinder 2 and inverted, that assembly being then supported with the exposed lower surface of the wall 6 isolated from the floor or other support so that it does not become adulterated.

Figure 9:
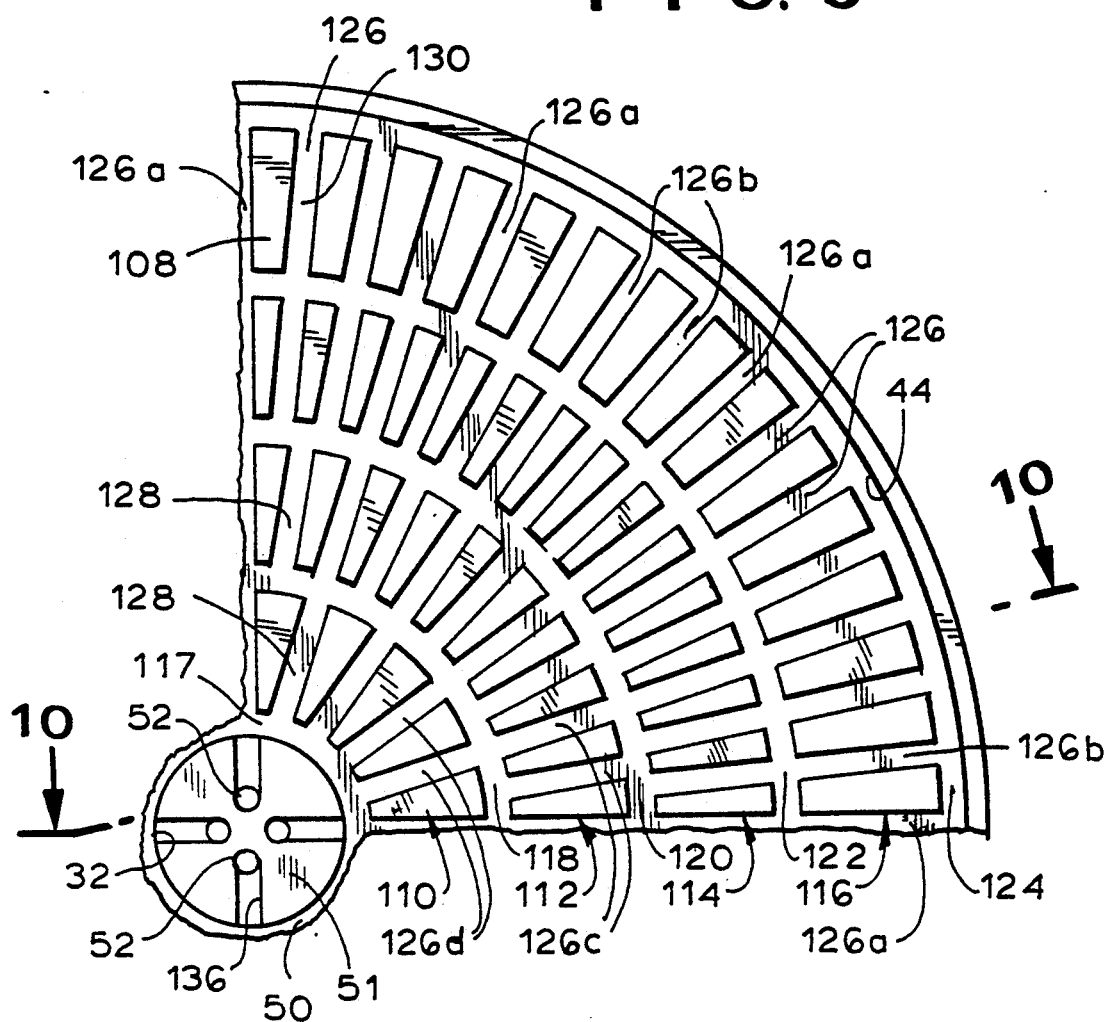
FIG. 9 is a view similar to FIG. 7 but showing a portion of the column-facing surface of the upper column wall.
Figure 10:
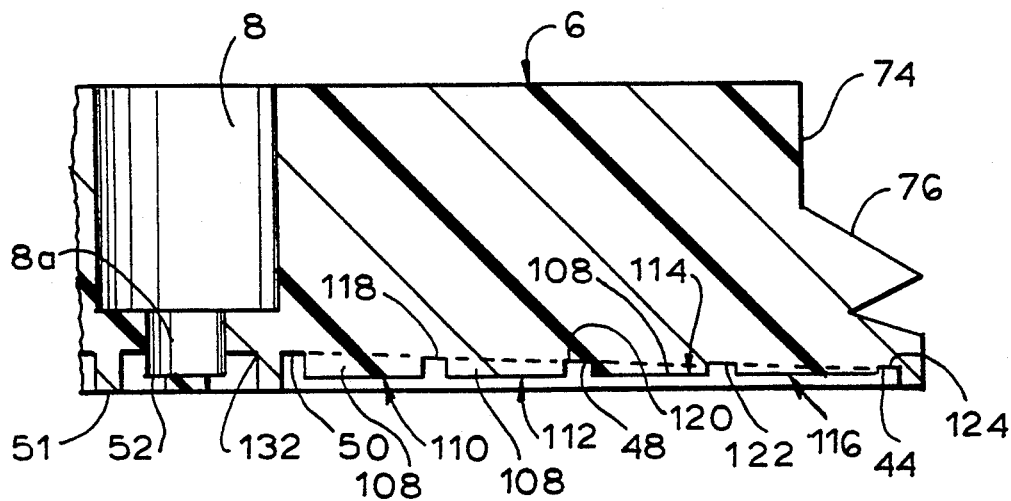
FIG. 10 is a cross-sectional view taken along the line 10—10 of FIG. 9.

It has been pointed out that relatively uniform distribution of the mobile phase over the entire cross-sectional area of the column is very desirable. In accordance with the present invention, such uniform liquid distribution is maximized by the shaping of the lower surface 42 of the wall 6, details of which can beest be seen in FIGS. 9 and 10. The wall sections 44, 48 and 50 produce a concavity which may be considered as comprising a first space of uniform thickness across the face of the wall, defined by the wall section 44 and into which the filter 46 is received, and a second space the depth of which varies in a radial direction as defined by the wall sections 48 and 50, the depth of that space decreasing as one moves radially outwardly. That space is partially filled by a series of lands 108 preferably arranged as shown in FIGS. 9 and 10. The lands are arranged in a series of circumferential rings 110, 112, 114 and 116 radially separated by circumferential grooves 118, 120 and 122, the radially outermost land sections being separated from the wall surface 44 by a circumferential groove 124. The exposed faces of the lands 108 are in a plane, as may be seen from FIG. 10, thereby to provide support for the filter 46. The lands of each set are separated by essentially radially oriented grooves 126. Preferably the lands in ring 110 have a maximum width greater than that of the lands in rings 112, 114 and 116, the lands in ring 116 are wider than the lands in rings 112 and 114, and all of the lands are tapered. The lands are so arranged in their several groups that in some instances there are radial grooves 126a extending uninterruptedly from the center of the wall to the circumferential groove 124, while other radial grooves 126b extend from the circumferential groove 120 to the circumferential groove 124, and some of the grooves 126c separating the lands of ring 112 are circumferentially aligned with end faces of the lands of ring 110. The grooves 126d between the lands of ring 110 communicate radially with grooves 128b extending all the way to the circumferential groove 124. The center of the wall 6, where it communicates with the entrance orifice 8, has a hole 132 filled by the plug 51 provided with the apertures 52, those apertures in turn communicating with radial grooves 136 in the lower face of the plug 51 which are preferably aligned with some of the radially extending grooves 126b which extend uninterruptedly to the circumferential groove 124. A circumferential groove 117 is formed between the plug 51 and the lands of ring 110. It has been found that best results are achieved when the volume of the constant volume section within which the filter 46 is received is approximately twice that of the variable volume section. It has further been found that best results are achieved if the width of a land 108 is no greater than four times the width of the grooves 126 alongside it. The taper in the height of the variable volume section is preferably one dimension unit change in height for four units of radial distance.

The lands 108 provide support surfaces for the filter 46, thus preventing separation of a packing bed support from the column bed. They reduce the volume of dead space above the filter plate, thus minimizing the possibility of sample stagnation and mixing and increasing the resolution and hence efficiency of the column. The configuration and arrangement of the lands and grooves, also preferably together with the radial flow direction achieved by the holes 52 and grooves 136 in the plug 51, maximize distribution of feed above the filter plate. The fluid will seek the easier radial flow path rather than the restricted flow through the filter 46, thus establishing a radial distribution of the fluid prior to any vertical flow through the bed. The plug 51 effectively prevents any axial jet-type flow from the inlet opening 8a and converts that axial flow into a radial flow which is accurately directed toward the lands and grooves which produce the desired result. The circumferential grooves 117, 118, 120, 122 and 124 provide pressure equalization, giving rise to effective fluid communication at a constant radius and preventing any sector formation in the vertical plane of the column. Uniform pressure along a radius of the bottom wall ensures a constant pressure differential and a constant flow velocity between the center of the wall and any point on a radius, thus ensuring constant flow volume in all directions from the center and hence better resolution. The outermost circumferential groove 124 provides a barrier for breaking up any streams of fluid coming through the grooves 126, thus preventing jet effects.

This design has the following advantages, among others: minimized chamber volume to prevent mixing of samples; uniform distribution in the horizontal plane to minimize cone or trunk formation due to jet velocity; uniform fluid distribution in the vertical plane through the column for better resolution; minimum resistance to flow in the distribution chamber provided by the lands and grooves.

The bottom wall 4 has a column-facing surface which is in some respects similar to that of the column-facing surface of the top wall 6, in that it comprises a constant volume section 138 adapted to receive a filter and a concave section 140 which has a tapered thickness decreasing as one moves radially outwardly. Three rings of lands 142, 144 and 146 are formed on that tapering surface, the upwardly facing surfaces of those lands being in a plane so as to provide support for the filter. Land rings 142 and 144 are separated by circumferential groove 148, land rings 144 and 146 are separated by a very wide circumferential groove 150, and circumferential groove 152 is provided between the radially outer lands of the ring 146 and the rim 154.

The configuration of the lands and grooves on the column-facing surface of the bottom wall 4 is different from that of the column-facing surface of the top wall 6 because at the bottom of the column the problems presented are different from those at the top of the column. Although the land-groove configurations here shown for the bottom wall 4 could be used on a top wall 6 for distribution of flow over the entire cross-sectional area, that configuration is less efficient in that regard than the configuration here specifically disclosed for the top wall 6. The land-groove configuration of the bottom wall 4, however, is more efficient than that here disclosed for the column-facing surface of the top wall 6 insofar as its function—sample collection—is concerned. The tapered nature of the recess 140 formed in the column-facing surface of the bottom wall 4, with the greatest depth being at the center, compensates for increased volume of sample collected as the flow travels toward the center of the wall, thus maintaining a substantially uniform velocity of fluid flow over the plate surface which in turn eliminates jet formation at the outlet opening 10, giving rise to better resolution of the sample. The specific shaping of the lands 142, 144 and 146, and in particular their tapering and the diamond-like configuration of the lands of rings 142 and 144, reduces stagnation points and hence dead space, and the lands formed thereby will still provide effective support for the filter.

The land-groove configurations on the column-facing surfaces of the column end walls are carefully designed to produce optimum overall results. Providing the circumferentially extending grooves between sets of lands and between the radially outermost sets of lands and the rim defining the outer limit of the liquid-receiving space is particularly important in that regard, as is, for the top wall involved in initial liquid distribution, the conversion of the axial liquid flow into radial liquid flow by means of the plug 51 and the alignment of those radial flows with selected grooves between lands.

By reason of the individual and combined effects of the structural elements here disclosed, an improved chromatography column has been devised which can be readily adapted to produce columns of different heights, where the manipulations involved in so adjusting the column height are made easier and more rapid, and where the structure not only facilitates such operation but also ensures that when the top column wall is removed it can be safely put aside. In addition, and most importantly, particularly but not exclusively when the column is to be used for preparative separations, the column-facing surfaces of the column end walls are provided with specific arrangements of lands and grooves by reason of which fluid flow over those faces is optimized for the respective functions of the top wall 6—uniform fluid supply over the full cross-sectional area of the column—and the bottom wall 4—minimum flow resistance and elimination of stagnation points.

While but a single embodiment of the present invention has been here specifically disclosed, it will be apparent that many variations may be made therein, all within the spirit of the invention as defined in the following claims.

We claim:

1. In a chromatography column comprising a column-producing wall and spaced top and bottom closures in and sealingly engaging said wall to define the extremes of said column, said closures having fluid ports therethrough, at least one of said closures comprising a distribution plate through which one of said ports extends, said plate having a column-facing surface, and a filter medium secured to said closure and extending over said column-facing surface thereof, said column-facing surface having radially oriented fluid passages formed thereon for distributing said fluid radially over said filter medium, the improvement which comprises said radially oriented fluid passages on said surfaces decreasing in depth while progressing radially outwardly and being formed into a plurality of passage sections, each said section essentially circumferentially disposed around said fluid port and said sections being radially located with respect to one another, the passages of each section being radially separated by and communicating with a circumferential fluid passage section, thereby to produce a constant pressure differential and a constant flow velocity between the center of the wall and any point on a radius, thus ensuring constant flow volume in all directions from the center and hence better resolution.

2. The chromatography column of claim 1, in which the passages of one section are aligned with the passages of the next adjacent section.

3. The chromatography column of claim 1, in which only some of the passages of one section are aligned with the passages of the next adjacent section.

4. The chromatography column of claim 1, in which the passages of each of said sections are of substantially the same width.

5. The chromatography column of claim 1, in which the passages of at least two of said sections are of different widths.

6. The chromatography column of claim 1, in which the passages in said sections are of substantially the same width and in which at least some of the passages in one section are out of alignment with the passages of the next adjacent section.

7. The chromatography column of claim 1, in which, on the closure at the top of said column the passages in each of said sections are of substantially the same width, and on the closure at the bottom of said column the passages in at least two radially adjacent sections are of different widths.

8. The chromatography column of any of claims 1–7, in which said fluid port comprises means aligned with at least some of said radially oriented fluid passages on said column-facing surface which direct fluid which enters said port into a plurality of separate generally radially oriented flows which enter said radially oriented fluid passages.

9. In a chromatography column comprising a column-producing wall and spaced top and bottom closures in and sealingly engaging said wall to define the extremes of said column, said closures having fluid ports therethrough, at least one of said closures comprising a distribution plate through which one of said fluid ports extends, said plate having a column-facing surface, and a filter medium secured to said closure and extending over said column-facing surface thereof, said column-facing surface having radially oriented passages formed thereon for distributing said fluid laterally over said filter medium, the bottom surfaces of said passages producing a space which deepens from radially outward to radially inward position, the improvement which comprises said laterally oriented fluid passages on said surface being formed into a plurality of passage sections, each said section essentially circumferentially disposed around said fluid port and said sections being radially located with respect to one another, the passages in one section having radially tapering side walls, and in which a circumferential fluid passage section is radially interposed between two of said sections, thereby to produce a substantially uniform pressure differential between said fluid port and radially outwardly located points on said plate.

10. The chromatography column of claim 9, in which a circumferential fluid passage section of width greater than that of said radial grooves is radially interposed between two of said sections.

11. The chromatography column of claim 9, in which there are at least three sections of laterally oriented fluid passages, the circumferential fluid passage radially inside the radially outermost of said sections being of given width, the circumferential fluid passage radially outside the radially innermost of said sections being of lesser width.

* * * * *